United States Patent [19]

Böwing et al.

[11] 4,051,058

[45] Sept. 27, 1977

[54] STABLE PEROXY-CONTAINING MICROBICIDES

[75] Inventors: Walter Grosse Böwing; Hinrich Mrozek, both of Dusseldorf; Hans-Joachim Schlüssler, Haan; Bernd Tinnefeld, Velbert; Peter Vögele, Sindelfingen, all of Germany

[73] Assignee: Henkel & Cie GmbH, Dusseldorf-Holthausen, Germany

[21] Appl. No.: 711,205

[22] Filed: Aug. 3, 1976

[30] Foreign Application Priority Data

Aug. 16, 1975 Germany .............................. 2536618
Apr. 12, 1976 Germany .............................. 2616049

[51] Int. Cl.$^2$ .................... A61K 33/40; A61K 7/135; C11D 7/18; C11D 7/38
[52] U.S. Cl. ...................................... 252/186; 252/95; 260/610 A; 423/272; 424/130
[58] Field of Search ................. 252/186, 95; 424/130, 424/223, 62; 260/610 A; 423/272, 273

[56] References Cited

U.S. PATENT DOCUMENTS

| 3,684,477 | 8/1972 | Blumbergs et al. ................... 424/130 |
| 3,864,271 | 2/1975 | Stalter ................................... 252/186 |
| 3,907,991 | 9/1975 | Accetta ................................. 424/130 |

*Primary Examiner*—Benjamin R. Padgett
*Assistant Examiner*—Irwin Gluck
*Attorney, Agent, or Firm*—Hammond & Littell

[57] ABSTRACT

Stable peroxy-containing concentrates useful for the production of microbicidal agents consisting essentially of 0.5% to 20% by weight of peracetic or perpropionic acid or their precursors,
25% to 40% by weight of $H_2O_2$,
0.25% to 10% by weight of an organic phosphonic acid capable of sequestering bivalent metal cations and their water-soluble acid salts,
0 to 5% by weight of anionic surface-active compounds of the sulfonate and sulfate type,
remainder: water.

9 Claims, No Drawings

STABLE PEROXY-CONTAINING MICROBICIDES

RELATED ART

It is known that the solutions of peracetic acid and perpropionic acid have microbicidal properties, peracetic acid being preferably employed. The pure peracids are difficult to handle. This difficulty arises not only with regard to their production, but also because they are a fire and explosion hazard. For this reason the peracids were not used in practice in pure form, but in mixtures such as 35% to 45% of peracetic acid, for example, and 40% to 55% of acetic acid. The amount of water present is generally below 15%. The disadvantage of these concentrates is that they can only be handled under strict safety measures, because of their pungent odor and their corrosive effect on the user who must at first dilute the concentrates.

OBJECTS OF THE INVENTION

An object of the present invention is the development of a stable peroxy-containing concentrate useful for the production of microbicidal agents which is safe to handle and not unduly corrosive to human skin.

Another object of the present invention is the development of a stable peroxy-containing concentrate useful for the production of microbicidal agents consisting essentially of 1. from 0.5% to 20% by weight of an acid selected from the group consisting of peracetic acid, acetic acid, mixtures of peracetic acid and acetic acid, perpropionic acid, propionic acid and mixtures of perpropionic acid and propionic acid, 2. from 25% to 40% by weight of $H_2O_2$ 3. from 0.25% to 10% by weight of a sequestering compound selected from the group consisting of an organic phosphonic acid capable of sequestering bivalent metal cations and its water-soluble acid salt, 4. from 0 to 5% by weight of an anionic surface-active compound selected from the group consisting of sulfonates and sulfates, and 5. the remainder to 100% by weight, water.

These and other objects of the invention will become more apparent as the description thereof proceeds.

DESCRIPTION OF THE INVENTION

It was now found that the above objects can be achieved and the disadvantages recited above can be avoided, and stable peroxy-containing concentrates for the production of microbicidal agents of increased effectiveness, based on aliphatic monopercarboxylic acids, can be obtained. These concentrates of the invention are characterized by a content of 0.5% to 20% by weight of a peracid with 2 to 3 carbon atoms and/or their corresponding aliphatic monocarboxylic acids, 25% to 40% by weight of $H_2O_2$, as well as 0.25% to 10% by weight of a phosphonic acid or its acid salts, with the balance, water.

More particularly, the invention relates to a stable peroxy-containing concentrate useful for the production of microbicidal agents consisting essentially of 1. from 0.5% to 20% by weight of an acid selected from the group consisting of peracetic acid, acetic acid, mixtures of peracetic acid and acetic acid, perpropionic acid, propionic acid and mixtures of perpropionic acid and propionic acid, 2. from 25% to 40% by weight of $H_2O_2$ 3. from 0.25% to 10% by weight of a sequestering compound selected from the group consisting of an organic phosphonic acid capable of sequestering bivalent metal cations and its water-soluble acid salt, 4. from 0 to 5% by weight of an anionic surface-active compound selected from the group consisting of sulfonates and sulfates, and 5. the remainder to 100% by weight, water.

Preferably the stable peroxy-containing concentrates contain from 5% to 10% by weight of component (1), from 0.5% to 5% of component (3), and a molar excess of $H_2O_2$ with reference to acid component (1), calculated as the monocarboxylic acid, in a molar ratio of at least 2:1, preferably from 3:1 to 50:1. When the anionic surface-active compound of the sulfonate and sulfate type is present, it is preferably in an amount of from 0.5% to 5% by weight.

The sequestering phosphonic acids of component (3) are those which can sequester bivalent metal cations, particularly calcium. A great number of phosphonic acids are thus suitable, which can also contain carboxyl groups, apart from the phosphonic acid groups. Preferably, however, the phosphonic acids are low molecular weight aliphatic compounds containing at least two anion groups, at least one of which is a phosphonic acid group. Among these are the diphosphonic acids having the formulae

and

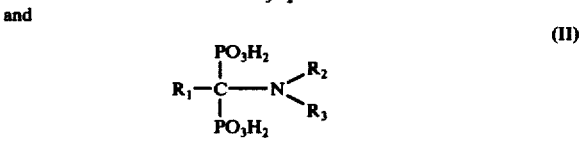

wherein $R_1$ is a member selected from the group consisting of phenyl, cycloalkyl having 5 to 6 carbon atoms and alkyl having 1 to 6 carbon atoms, $R_2$ and $R_3$ are members selected from the group consisting of hydrogen, alkyl having 1 to 4 carbon atoms and aminoalkyl having 1 to 4 carbon atoms. The following are a number of operable phosphonic acids:

aminotri-(methylene phosphonic acid)
dimethylaminomethane diphosphonic acid
aminoacetic acid-N-di-(methylene phosphonic acid)
ethylenediamine-tetra-(methylene phosphonic acid)
1-amino-1-cyclohexylmethane-1,1-diphosphonic acid
1-(N-methylamino)-ethane-1,1-diphosphonic acid
3-aminopropane-1-hydroxyl-1,1-diphosphonic acid
2-phosphonobutane-1,2,4-tricarboxylic acid
ethylenediamine-tetra-(methylene phosphonic acid)
phosphonosuccinic acid
1-phosphono-1-methylsuccinic acid Particularly suitable phosphonic acids are:
dimethylaminomethane diphosphonic acid
1-amino-1-phenylmethane diphosphonic acid
aminotri-(methylene phosphonic acid)
aminoacetic acid-N-di-(methylene phosphonic acid)
1-hydroxyethane-1,1-dkphosphonic acid The above-mentioned phosphonic acids can also be used in the form of their acid water-soluble salts, particularly the alkali metal salts, such as sodium or potassium; the ammonium salts or the alkylol amine salts where the alkylol has 2 to 3 carbon atoms, such as mono-, di- or tri-ethanolamine salts. If desired, mixtures of the individual phosphonic acids or their acid salts can also be used. The acid salts are partial salts of the phosphonic acids having an acid pH in aqueous solutions.

The production is effected in a simple manner by mixing an $H_2O_2$ solution, preferably with a concentration of about 33% by weight, with the peracid, such as peracetic acid and, optionally, acetic acid, in the presence of the phosphonic acid. The mixtures can also be produced in an advantageous manner by merely adding the corresponding amounts of peracid, such as acetic acid, and phosphonic acid to the concentrated $H_2O_2$ solution.

Since the products mainly are not used immediately, but are first stored, a corresponding amount of peracetic acid is formed when acetic acid is employed. The formation of peracetic acid can be accelerated catalytically, if desired, by adding a small amount of a mineral acid (0.1% to 1% by weight). In general, however, such an addition is not necessary for the above-mentioned reasons.

Such concentrates, which are produced, for example, from 30% by weight of $H_2O_2$, 5% by weight of acetic acid, 3% by weight of phosphonic acid, and 62% by weight of water, have no annoying odor and are easy to handle. They can be diluted easily to concentrations of 0.1% to 1%, as they are used in food technology and in the medical field, without requiring special precautions. The solutions also have a good microbial effect in great dilution.

The preparations have beyond that the advantage, due to the amount of $H_2O_2$, that they have a long term effect on most microorganisms. They are, therefore, also suitable for static disinfection to prevent the secondary growth of germs on machines, after cleaning, particularly in the food industry.

In some cases it has been found of advantage to add wetting agents to the preparations in order to further improve the desired properties. It was found that concentrates which are stable in storage can be obtained if anionic surface-active compounds of the sulfonate and sulfate type, such as alkylbenzene sulfonates having 6 to 18 carbon atoms in the alkyl, alkyl sulfates and/or alkane sulfonates (each having 8 to 22 carbon atoms in the alkyl or alkane group), are added in amounts of 0.05% to 5% by weight.

The alkylbenzene sulfonates which can be employed are preferably those which contain an alkyl radical of 6 to 18 carbon atoms, preferably 9 to 15 carbon atoms. Instead of the alkylbenzene sulfonates, alkyl sulfates or alkane sulfonates with an alkyl or alkane radical of the chain length of 12 to 18 carbon atoms, can be employed. If desired, mixtures of the above-mentioned anionic surface-active compounds can naturally also be used.

It was found that, with the above-mentioned additives, the concentrates remain stable over long periods of time and that the content of peracetic acid in the concentrate thus also remains constant. However, if soaps or the conventional non-ionic surface-active compounds are employed as the surface-active additive, a sufficient stability is not achieved.

The following examples are illustrative of the invention without being limitative in any manner.

EXAMPLE 1

Concentrates were produced containing 33% by weight of $H_2O_2$, 5% by weight of acetic acid, 0.5% by weight of the phosphonic acid listed, and the balance water.

The following phosphonic acids were employed in the individual concentrates:
A. dimethylaminomethane diphosphonic acid
B. 1-amino-1-phenylmethane diphosphonic acid
C. aminotri-(methylene phosphonic acid)
D. aminoacetic acid-N-di-(methylene phosphonic acid)
E. 1-hydroxyethane-1,1-diphosphonic acid
F. 1-amino-1-cyclohexylmethane-1,1-diphosphonic acid
G. 1-(N-methylamino)-ethane-1,1-diphosphonic acid
H. ethylenediaminetetra-(methylene phosphonic acid)

In order to obtain a comparison value, no phosphonic acid was added to another concentrate.

The concentrates were left standing for about a week and then diluted to a concentration of 0.1%. The microbicidal activity was determined in the suspension test according to the guidelines of Deutsche Gesellschaft for Hygiene und Mikrobiologie (DGHM). Staphylococcus aureus and Escheria coli were employed as test microorganisms.

The killing time in minutes is given in Table I.

TABLE I

| Phosphonic Acid Additive | Killing Time in Minutes | |
|---|---|---|
| | S. aureus | E. coli |
| Without | 10 | 60 |
| A | 1 | 10 |
| B | 1 | 10 |
| C | 1 | 20 |
| D | 1 | 20 |
| E | 1 | 20 |
| F | 5 | 40 |
| G | 5 | 40 |
| H | 5 | 40 |

EXAMPLE 2

Stable concentrates were produced containing 33% by weight of $H_2O_2$, 5% of acetic acid, 1%, 3% or 5% of either phosphoric acid (control), 1-hydroxyethane-1,1-diphosphonic acid, or 2-phosphonobutane-1,2,4-dicarboxylic acid, the balance water. The concentrates were left standing for 8 days and then diluted to a concentration of 0.05%.

The microbial activity was determined on the basis of the germ reduction and reported as "D". The following testing method was used:

0.1 ml of a germ suspension (number of germ $10^8$/ml) were added to 10 ml disinfecting solution (or to a control of 10 ml of water). The mixture was stirred for five minutes, 0.1 ml were removed and put into 10 ml of deinhibiting solution (0.5% aqueous thiosulfate solution). The number of germs was determined after fifteen minutes according to Koch's plate method.

The evaluation was made according to the formula:

$$"D" = \log \frac{\text{Number of germs in the control}}{\text{Number of germs in the disinfecting solution}}$$

"D" thus indicates the reduction of germs quantitatively in logarithmic form, e.g., "D" = 1, means that the number of germs was reduced by 1 decimal power (or factor).

The comparison value with an addition of phosphoric acid shows that the influence of the acidity of the added phosphonic acid is not a factor.

TABLE II

| "D" Values | | % Additive | |
|---|---|---|---|
| E. coli | Pseudomonas aeruginosa | | |
| 0.5 | 2.0 | 1 | |
| 0.4 | 2.3 | 3 | phosphoric acid |
| 0.5 | 2.5 | 5 | |
| 3.0 | over 4.8 | 1 | |
| 2.2 | over 4.8 | 3 | 1-hydroxyethane-1,1-diphosphonic acid |
| over 5.3 | over 4.9 | 5 | |
| 0.9 | 3.5 | 1 | |
| 1.0 | over 4.8 | 3 | 2-phosphonobutane-1,2,4-tricarboxylic acid |
| over 4.9 | over 4.8 | 5 | |

NOTE: "Over" in front of the "D" values means that all germs were killed.

EXAMPLE 3

A concentrate for the production of microbicides was prepared by mixing:

| Percent by Weight | |
|---|---|
| 5 | Acetic acid |
| 27.5 | $H_2O_2$ |
| 1.5 | Hydroxyethane-1,1-diphosphonic acid |
| 1.5 | Alkyl-C-12)-benzenesulfonate, as well as |
| 64.4 | Water |

The concentrate was divided into two parts and left standing at temperatures of 20° and 40° C. Samples were taken at certain intervals to determine the content of $H_2O_2$ and peracetic acid. The results are compiled in Table III. It can be seen clearly that the concentrates are stable over long periods of time even in the presence of the above indicated wetting agent.

TABLE III

Content of hydrogen peroxide and peracetic acid at 20° C and 40° C as a function of time

| Temp. | Time | % $H_2O_2$ | % Peracetic Acid |
|---|---|---|---|
| 20° C | Initial value | 28.3 | 2.3 |
| | 8 days | 28.1 | 2.3 |
| | 1 month | 27.5 | 2.3 |
| | 3 months | 27.3 | 2.3 |
| | 6 months | 26.5 | 2.3 |
| 40° C | Initial value | 28.8 | 2.2 |
| | 8 days | 27.8 | 2.2 |
| | 1 month | 26.8 | 2.2 |
| | 3 months | 26.7 | 2.2 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A stable peroxy-containing concentrate useful for the production of microbicidal agents consisting essentially of
   1. from 0.5% to 20% by weight of an acid selected from the group consisting of peracetic acid, acetic acid, mixtures of peracetic acid and acetic acid, perpropionic acid, propionic acid and mixtures of perpropionic acid and propionic acid,
   2. from 25% to 40% by weight of $H_2O_2$,
   3. from 0.25% to 10% by weight of a sequestering compound selected from the group consisting of an organic phosphonic acid capable of sequestering bivalent metal cations and its water-soluble acid salt,
   4. from 0 to 5% by weight of an anionic surface-active compound selected from the group consisting of sulfonates and sulfates, and
   5. the remainder to 100% by weight, water.

2. The stable peroxy-containing concentrate of claim 1 wherein component (1) is present in an amount of from 5% to 10% by weight, component (3) is present in an amount of from 0.5% to 5% by weight, and said $H_2O_2$ of component (2) is present in a molar excess with reference to said acid of component (1), calculated as the monocarboxylic acid of a molar ratio of at least 2:1.

3. The stable peroxy-containing concentrate of claim 2 wherein said molar ratio of $H_2O_2$ to monocarboxylic acid is from 3:1 to 50:1.

4. The stable peroxy-containing concentrate of claim 3 wherein said component (4) is pesent in an amount of from 0.5% to 5% by weight.

5. The stable peroxy-containing concentrate of claim 4 wherein said anionic surface-active compound is selected from the group consisting of alkylbenzene sulfonates having from 6 to 18 carbon atoms in the alkyl, alkane sulfonates having from 8 to 22 carbon atoms in the alkane, and alkyl sulfates having from 8 to 22 carbons atoms in the alkyl.

6. The stable peroxy-containing concentrate of claim 1 wherein said component (4) is present in an amount of from 0.5% to 5% by weight.

7. The stable peroxy-containing concentrate of claim 6 wherein said anionic surface-active compound is selected from the group consisting of alkylbenzene sulfonates having from 6 to 18 carbon atoms in the alkyl, alkane sulfonates having from 8 to 22 carbon atoms in the alkane, and alkyl sulfates having from 8 to 22 carbon atoms in the alkyl.

8. The stable peroxy-containing concentrate of claim 1 wherein said organic phosphonic acid capable of sequestering bivalent metal cations is a low molecular weight aliphatic compound containing at least two anion groups, at least one of which is a phosphonic acid group.

9. The stable peroxy-containing concentrate of claim 8 wherein said organic phosphonic acid capable of sequestering bivalent metal cations is a member selected from the group consisting of:
dimethylaminomethane diphosphonic acid,
1-amino-1-phenylmethane diphosphonic acid,
aminotri-(methylene phosphonic acid),
aminoacetic acid-N-di-(methylene phosphonic acid), and
1-hydroxyethane-1,1-diphosphonic acid.

* * * * *